United States Patent [19]

Matsumoto et al.

[11] 4,411,998
[45] Oct. 25, 1983

[54] SUPPRESSING METHOD OF ISO-CITRIC ACID FORMATION IN PRODUCING CITRIC ACID FROM HYDROCARBONS BY FERMENTATION

[75] Inventors: Takao Matsumoto; Atsushi Fujimaki; Takeo Nagata, all of Yokohama, Japan

[73] Assignee: Showa Oil Company, Ltd., Japan

[21] Appl. No.: 359,773

[22] Filed: Mar. 19, 1982

[51] Int. Cl.$^3$ .............................................. C12P 7/48
[52] U.S. Cl. .................................. 435/144; 435/248; 435/249; 435/923; 435/924
[58] Field of Search ....................... 435/144, 248–250, 435/923, 924

[56] References Cited

U.S. PATENT DOCUMENTS

| | | | |
|---|---|---|---|
| 3,372,094 | 3/1968 | Gold et al. | 435/144 |
| 3,691,012 | 9/1972 | Tanaka et al. | 435/144 |
| 3,773,620 | 11/1973 | Kimura et al. | 435/144 |
| 4,178,211 | 12/1979 | Leavitt | 435/144 |
| 4,180,626 | 12/1979 | Nagata et al. | 435/144 |

FOREIGN PATENT DOCUMENTS 1211246 11/1970 United Kingdom ................ 435/144

*Primary Examiner*—R. B. Penland
*Attorney, Agent, or Firm*—Oldham, Oldham, Hudak, Weber & Sand Co.

[57] ABSTRACT

The present invention relates to a suppressing method of iso-citric acid formation in producing citric acid from hydrocarbons by fermentation.

This process is carried out by culturing the microorganisms selected from the group belonging to *Candida tropicalis, Candida lipolytica, Candida intermedia* and *Candida brumptii* and their mutants and variants in the culture medium containing paraffinic and olefinic hydrocarbons and their mixture as carbon source under aerobic conditions, wherein specific non-ionic surface active agent is added to said culture medium.

The specific non-ionic surface active agent added to said culture medium is selected from the group of sorbitan fatty acid esters and polyoxy-ethylene sorbitan fatty acid esters. The amount of specific surface active agent added to said culture medium is enough from 0.005 to 0.5 percent by weight, preferably from 0.02 to 0.2 percent on the weight basis of said culture medium.

2 Claims, No Drawings

SUPPRESSING METHOD OF ISO-CITRIC ACID FORMATION IN PRODUCING CITRIC ACID FROM HYDROCARBONS BY FERMENTATION

BACKGROUND OF THE INVENTION

The present invention relates to a suppressing method of iso-citric acid formation in producing citric acid from hydrocarbons by fermentation.

It has been well known that citric acid is produced by the assimilation of normal paraffins as carbon source.

Furthermore, we, inventors, have proposed the production process of citric acid from normal α-olefins of $C_{8-40}$ as carbon source by culturing the microorganisms selected from the group of *Candida tropicalis, Candida intermedia* and *Candida brumptii* and their mutants and their variants, in U.S. Pat. No. 4,180,626.

Iso-citric acid is commonly accumulated in the citric acid fermentation using hydrocarbons as carbon source. The yield of iso-citric acid accumulated in the culture medium is often equal to or higher than that of citric acid, though said yield is somewhat different by the kinds of microorganisms and the cultural conditions.

We have discovered that the iso-citric acid formation in the citric acid production from hydrocarbons by ferementation is suppressed by adding the specific non-ionic surface active agents, such as sorbitan fatty acid esters and polyoxy-ethylene sorbitan fatty acid esters to said culture medium.

In general, the steric isomers are often produced in organic acid fermentations. For suppressing the formation of isomer and dominating the normal compound, some mutants have been commonly used. However, said method requires a great deal of work and cost in search of the mutants and in examination of the cultural conditions.

In the present invention, the formation of iso-citric acid can be suppressed by adding the specific non-ionic surface active agent to the culture medium, and any mutant is not required. This effect has a great industrial significance.

SUMMARY OF THE INVENTION

The main object of this invention is to provide a suppressing method of iso-citric acid formation in producing citric acid by culturing the microorganisms which are assimilable to paraffinic and olefinic hydrocarbons in the culture medium containing the specific non-ionic surface active agent under aerobic conditions.

Said object is accomplished by cultivating the microorganisms selected from the group of *Candida lipolytica, Candida tropicalis, Candida intermedia* and *Candida brumptii* and their auxotrophic mutants and their variants in the culture medium containing paraffins of $C_{10-18}$ and olefins of $C_{8-40}$ as carbon source.

The specific non-ionic surface active gents used in this invention are shown in Table 1.

TABLE 1

Surface active agents used in this invention
Sorbitan fatty acid esters and Polyoxy-ethylene sorbitan fatty acid esters

| Component | Molecular structure |
| --- | --- |
| Sorbitan monolaurate<br>Sorbitan monopalmitate<br>Sorbitan monostearate<br>Sorbitan tristearate<br>Sorbitan monooleate<br>Sorbitan trioleate<br>Sorbitan sesquioleate<br>Sorbitan distearate | $\begin{array}{c} \phantom{xx} O \\ H_2C \phantom{xx} CH-CH_2OOC.R \\ \phantom{x}\vert \phantom{xxx} \vert \\ HOHC \phantom{xx} CHOH \\ \phantom{xx} C \\ \phantom{xx} H \\ \phantom{xx} O \\ \phantom{xx} H \end{array}$ |
| Polyoxy-ethylene sorbitan monolaurate<br>Polyoxy-ethylene sorbitan monopalmitate<br>Polyoxy-ethylene sorbitan monostearate<br>Polyoxy-ethylene sorbitan tristearate<br>Polyoxy-ethylene sorbitan monooleate<br>Polyoxy-ethylene sorbitan trioleate | $\begin{array}{c} \phantom{xxxxxx} O \\ \phantom{xxxxx} H_2C \phantom{xxx} CHCH_2OOC.R \\ H_n(CH_2CH_2O)OHC \phantom{xx} CHO(CH_2CH_2O)_nH \\ \phantom{xxxxxx} C \\ \phantom{xxxxxx} H \\ \phantom{xxxxxx} \vert \\ \phantom{xxxxx} O(CH_2CH_2O)_nH \end{array}$ |

The amount of specific surface active agent added to the culture medium, though depending on the kind of said agent is enough from 0.005 to 0.5 percent on the weight basis of said medium, preferably 0.02–0.2 percent by weight is enough. Furthermore, it is desirable that said agent is added to the culture medium during from the initial phase to the logarithmic growth phase of cultivation, but it may be added to the culture medium at the initial phase of cultivation in case that a small amount of said agent is used.

In case of producing citric acid from hydrocarbons as carbon source, the amount of citric acid produced and the product ratio of citric acid to isocitric acid are dependent on the kind of carbon source (paraffins or olefins) and the composition of the culture medium, especially the kind of organic nutrients.

Paraffinic and olefinic hydrocarbons and their mixture may be used as carbon source for the fermentation process in this invention. Especially, olefinic hydrocarbons having carbon number of 8 or more are preferable. Particularly, it is the characeristic feature of this invention that olefins of $C_{14-40}$ unusable in the present market can be utilized.

Normal α-olefins are desirable olefins, but some iso- and inner-olefins are allowable to be used with normal α-olefins.

The concentration of said hydrocarbons in the culture medium is from 1 to 20 percent on the weight basis of said medium, preferably from 5 to 15 percent by weight. Comparing the melting point of olefins with that of paraffins of the same carbon number, olefins show lower melting point than paraffins, and as olefins have better dispersion property than paraffins of the same carbon number in the culture medium, it is advantageous to use olefins of $C_{14-40}$ in the culture medium as the carbon source.

As the nitrogen source of the culture medium, inorganic and organic ammonium salts, such as ammonium chloride, ammonium acetate, and various nitrogen compounds may be used individually or in mixture.

Ordinary inorganic salts such as phosphate, sulfate, hydrochloric acid salts, potassium salts, sodium salts, magnesium salts, iron salts, manganese salts, cupper salts and zinc salts may be used as inorganic nutrients in culture medium. Calcium carbonate and alkali compounds may be used to regulate pH of said medium. Biotin and thiamine as organic nutrients may be used in a trace amount individually or in their mixture, and also natural substances such as yeast extract or corn steep liquor containing biotin and thiamine may be used. When biotin and thiamine are used individually, the amount less than 1,000 µg/l of biotin or thiamine suffices to increase the production amount of citric acid. Even if the amount more than 1,000 µg/l of biotin or thiamine is used individually, the production amount of citric acid does not increase. Preferable amount of the organic nutrients is suitable from 50 to 100 µg/l. In case where both biotin and thiamine are added in said medium, the total amount of biotin and thiamine less than 1,000 µg/l, preferably 50–100 µg/l is enough to cultivate. In the process of this invention, α-olefin or mixture of olefins may be used as carbon source. These substrates are in liquid state at fermentation temperature.

DETAILED DESCRIPTION OF THE INVENTION

The effect of addition of specific non-ionic surface active agent to the culture medium in this invention will be explained later. The compositions of main culture medium are shown in Table 2.

TABLE 2

| The compositions of culture medium | | |
|---|---|---|
| | for Seed | for production |
| NH$_4$Cl | 6.5 g | 2.0 g |
| Na$_2$HPO$_4$.12H$_2$O | 1.5 g | — |
| KH$_2$PO$_4$ | 3.5 g | 0.5 g |
| MgSO$_4$.7H$_2$O | 0.5 g | 0.5 g |
| FeSO$_4$.7H$_2$O | 10 mg | 10 mg |
| MnSO$_4$.nH$_2$O | 0.1 mg | 0.1 mg |
| ZnSO$_4$.H$_2$O | 0.1 mg | 0.1 mg |
| CuSO$_4$.5H$_2$O | 5 µg | 5 µg |
| Yeast extract | 200 mg | — |
| Biotin | 100 µg | 100 µg |
| Thiamine.HCl | 100 µg | 100 µg |
| Deionized water | 1,000 ml | 1,000 ml |
| pH | 5.0 | 5.0 |

The cultural conditions are shown as follows:

Said microorganisms are cultivated under aerobic conditions. The fermentation temperature is in the range of 25° and 40° C., preferably about 30° C. pH value of said medium is in the range of 3–10, preferably 4–6. pH value of said medium is regulated by adding alkalis or salts such as sodium carbonate or calcium carbonate. The cultivation is ordinarily carried out for 50–150 hrs., preferably 80–100 hrs. Citric acid accumulated in said medium is isolated in the form of calcium citrate by normal method, for example, by filteration or by centrifugal method and then purified by chromatographic or ion exchange method.

Citric acid produced is recovered as follows:

Citric acid produced during the cultivation as described above is recovered in calcium salt form by filtering said medium using diatomaceous earth as a filter aid after conditioning pH to 2.0 with hydrochloric acid. The filter cake is washed with water and the washing water is combined with the clear filtrate and then heated after neutralizing the combined filtrate by caustic alkali. The combined filtrate is cooled and filtrated under the reduced pressure to recover calcium citrate. Calcium citrate produced is suspended into about 10 times volume of water, and heated in the boiling water for about 30 minutes after titrating with 50% of aqueous sulfuric acid solution until the filtrate slightly indicates the presence of sulfuric acid with addition of the aqueous solution of barium chloride to said filtrate. If necessary, the resulting solution is filtered while heating after decoloring said filtrate and concentrated under the reduced pressure at the temperature of 50°–60° C. During concentrating said filtrate, the precipitated calcium sulfate is filtered and continued to the concentration until the slightly washy sirup is obtained. When the sirup-like concentrated liquor is allowed to be cooled at 0° C., the crystalline of citric acid is obtained.

The analysis of citric acid, iso-citric acid and total citric acid was carried out as follows:

citric acid was recovered from the culture medium as the calcium salt.

The obtained salt was slurried with the distilled water and acidified to pH of less than 2 with hydrochloric acid to dissolve all soluble materials and was diluted with the distilled water to the predetermined volume.

The amount of citric acid contained in said obtained solution was quantitatively analyzed according to the colorimetric method using the reagent of pentabromacetone [Protein, Nucleic acid and Enzyme Bd. 2, Page 50 (1957) published by Kyoritsu Publishing Co., Tokyo].

Total citric acid (total amount of citric acid and iso-citric acid) was quantitatively analyzed according to the modified Saffran method [Journal of Agricultural Chemical Society of Japan Bd. 44 , Page 499 (1970)].

The amount of iso-citric acid was calculated by subtracting the amount of citric acid from the total amount of citric acid and iso-citric acid.

Hereinafter are described the examples of the present invention. The method of the present invention is not to be limited to the following examples.

EXAMPLE 1

The cultivation was carried out as follows:

*Candida tropicalis* IFO-0589 which had a good assimilability to olefinic hydrocarbon was used. n-Tetradecene-1 was used as carbon source in the concentration of 5 or 7 percent on the weight basis of said culture medium and polyoxy-ethylene sorbitan monooleate was added to said culture medium as surface active agent. The amount of said agent was varied to 0.02, 0.05 and 0.2 percent on the weight basis of said culture medium respectively. The seed of the microorganism described above was incubated in 500 ml Erlenmeyer flask containing 30 ml of said medium which was sterilized at 115° C. for 10 minutes and was allowed to be coold at 30° C. Said seed containing the microorganism belonging to *Candida tropicalis* was inoculated to said medium in the amount of 4 platinum wire loops.

The cultivation of seed was carried out at 30° C. on a reciprocating shaker operated at 120 oscills/minute with 7 cm strokes for 3 days. After about 16–18 hrs. from the beginning of the cultivation, 1% by weight of freshly sterilized calcium carbonate was added to said medium to regulate pH of about 5.0.

The production cultivation was carried out in 500 ml Erlenmeyer flask containing 30 ml of said medium and 5 percent of said seed on the volume basis of said medium for 6 days under the same conditions to those of the seed cultivation. 4% by weight of freshly sterilized calcium carbonate was added to said medium to regulate pH in the range of about 5.0. After cultivation, citric acid, iso-citric acid and total citric acid were analyzed according to said analytical method. The results were indicated in Table 3.

TABLE 3

Strain: *Candida tropicalis* IFO-0589
Carbon source: n-Tetradecene-1

| Amount of addition of surface active agent* (wt %) | Amount of citric acid (g/l) | Amount of iso-citric acid (g/l) | Amount of total citric acid (g/l) |
| --- | --- | --- | --- |
| Non-addition | 23.7 | 15.6 | 39.3 |
| 0.02 | 31.0 | 8.5 | 39.5 |
| 0.05 | 33.0 | 7.1 | 40.1 |
| 0.20 | 35.0 | 5.3 | 40.3 |

*polyoxy-ethylene sorbitan monooleate

EXAMPLE 2

It was clearly indicated in Example 2 that the production ratio of citric acid to iso-citric acid was influenced by the kinds of surface active agents. Polyoxy-ethylene sorbitan monolaurate (as A), polyoxyethylene sorbitan monooleate (as B), and sorbitan monooleate (as C) were added as surface active agent to said culture medium in concentration of 0.05 percent on the weight basis respectively.

As the microorganisms, *Candida lipolytica* IFO-0746 which had a good assimilability to n-paraffinic hydrocarbon was used to n-Tetradecane, and *Candida tropicalis* IFO-0589 which had a good assimilability to n-paraffinic and n-olefinic hydrocarbons was used to n-Tetradecane and n-Tetradecene-1 respectively, n-Tetradecane and n-Tetradecene-1 were used as carbon source in concentration of 5 or 7 percent on the weight basis of said culture medium respectively. The cultivations were carried out under the same procedures as those of Example 1.

The results were indicated in Tables 4–6.

TABLE 4

Strain: *Candida lipolytica* IFO-0746
Carbon source: n-Tetradecane

| Kind of surface active agents | Amount of citric acid (g/l) | Amount of iso-citric acid (g/l) | Amount of total citric acid (g/l) |
| --- | --- | --- | --- |
| Non-addition | 10.0 | 6.0 | 16.0 |
| B | 15.0 | 0 | 15.0 |
| C | 12.0 | 0 | 12.0 |

TABLE 5

Strain: *Candida tropicalis* IFO-0589
Carbon source: n-Tetradecene-1

| Kind of surface active agents | Amount of citric acid (g/l) | Amount of iso-citric acid (g/l) | Amount of total citric acid (g/l) |
| --- | --- | --- | --- |
| Non-addition | 23.7 | 15.6 | 39.3 |
| B | 31.8 | 0.7 | 32.5 |
| A | 29.3 | 1.4 | 30.7 |
| C | 32.8 | 0 | 32.8 |

TABLE 6

Strain: *Candida tropicalis* IFO-0589
Carbon source: n-Tetradecane

| Kind of surface active agents | Amount of citric acid (g/l) | Amount of iso-citric acid (g/l) | Amount of total citric acid (g/l) |
| --- | --- | --- | --- |
| Non-addition | 21.0 | 25.0 | 46.0 |
| C | 27.5 | 12.0 | 39.5 |
| B | 27.5 | 10.0 | 37.5 |

As shown in Examples 1 and 2, the suppressing effect on iso-citric acid formation in producing citric acid from hydrocarbons by fermentation was proved by the addition of the specific non-ionic surface active agent to the culture medium containing *Candida tropicalis* and *Candida lipolytica*. Furthermore in the cultivation of other microorganisms, that is, *Candida intermedia, Candida brumptii*, the same suppressing effect on isocitric acid formation was observed.

What is claimed is:

1. A method for suppressing iso-citric acid formation in producing citric acid from hydrocarbons by fermentation, comprising the steps of:
   providing microorganisms selected from the group consisting of *Candida tropicalis, Candida lipolytica, Candida intermedia* and *Candida brumptii* and their mutants and their variants;
   adding said microorganisms to a culture medium containing olefinic hydrocarbons; further adding to said medium from 0.005 to 0.5 percent on a weight basis of said culture medium of surface active agent selected from the group consisting of polyoxyethylene sorbitan monooleate, polyoxyethylene sorbitan monolaurate and sorbitan monooleate; and
   culturing said microorganisms under aerobic conditions to produce a mixture of citric acid and isocitric acid, wherein the ratio of citric to isocitric acid is at least 2:1.

2. A method according to claim 1, wherein the amount of said surface active agent is from about 0.02 to about 0.2 weight percent of said nutrient system.

* * * * *